(12) United States Patent
Armstrong

(10) Patent No.: US 7,974,701 B2
(45) Date of Patent: Jul. 5, 2011

(54) DOSING LIMITATION FOR AN IMPLANTABLE MEDICAL DEVICE

(75) Inventor: Randolph K. Armstrong, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 788 days.

(21) Appl. No.: 11/741,096

(22) Filed: Apr. 27, 2007

(65) Prior Publication Data
US 2008/0269839 A1 Oct. 30, 2008

(51) Int. Cl.
*A61N 1/08* (2006.01)
(52) U.S. Cl. .................. 607/59; 607/7; 607/30; 607/60
(58) Field of Classification Search ............ 607/2, 7–15, 607/27–32, 45–46, 57–64, 115–120, 145–150; 128/419
See application file for complete search history.

(56) References Cited

U.S. PATENT DOCUMENTS

| | | |
|---|---|---|
| 3,760,812 A | 9/1973 | Timm et al. |
| 3,796,221 A | 3/1974 | Hagfors |
| 4,107,469 A | 8/1978 | Jenkins |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara ........................ 128/784 |
| 4,577,316 A | 3/1986 | Schiff |
| 4,590,946 A | 5/1986 | Loeb |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |

(Continued)

FOREIGN PATENT DOCUMENTS

CA 2339971 6/2004
(Continued)

OTHER PUBLICATIONS

Bachman, D.,S. et al.; "Effects Of Vagal Volleys And Serotonin On Units Of Cingulate Cortex in Monkeys;" Brain Research, vol. 130 (1977). pp. 253-269.

(Continued)

*Primary Examiner* — Carl H Layno
*Assistant Examiner* — Paula J Stice
(74) *Attorney, Agent, or Firm* — Chowdhury, Georgakis, P.C.; Jonathan D. Rowell; Darrell N. Fuller

(57) ABSTRACT

A method for limiting patient-initiated electrical signal therapy to a cranial nerve of a patient is provided. An electrical signal therapy limit is selected from the group consisting of; a maximum number of patient-initiated signals, a maximum dose of electrical signals, a maximum duration of electrical signal, a maximum rate of change of the number of patient-initiated signals, a maximum rate of change of the dose of electrical signals, and a maximum rate of change of the duration of the electrical signals all per unit of time. If the electrical signal therapy limit is exceeded a therapy is delivered to the cranial nerve selected from the group consisting of; providing therapy, providing reduced therapy, providing enhanced therapy, inhibiting therapy, providing background therapy, and inhibiting background therapy.

15 Claims, 5 Drawing Sheets

U.S. PATENT DOCUMENTS

| | | | |
|---|---|---|---|
| 4,628,942 A | 12/1986 | Sweeney et al. | |
| 4,649,936 A | 3/1987 | Ungar et al. | |
| 4,702,254 A | 10/1987 | Zabara | 128/421 |
| 4,735,204 A * | 4/1988 | Sussman et al. | 607/60 |
| 4,793,353 A | 12/1988 | Borkan | |
| 4,867,164 A | 9/1989 | Zabara | 128/421 |
| 4,920,979 A | 5/1990 | Bullara | |
| 4,949,721 A | 8/1990 | Toriu et al. | |
| 4,977,895 A | 12/1990 | Tannenbaum | |
| 4,979,511 A | 12/1990 | Terry, Jr. | 128/642 |
| 5,025,807 A | 6/1991 | Zabara | 128/421 |
| 5,081,987 A | 1/1992 | Nigam | |
| 5,154,172 A | 10/1992 | Terry, Jr. et al. | 128/419 R |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,222,494 A | 6/1993 | Baker, Jr. | |
| 5,231,988 A | 8/1993 | Wernicke et al. | |
| 5,235,980 A | 8/1993 | Varrichio et al. | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | 607/2 |
| 5,330,507 A | 7/1994 | Schwartz | |
| 5,330,515 A | 7/1994 | Rutecki et al. | |
| 5,334,221 A | 8/1994 | Bardy | |
| 5,354,320 A | 10/1994 | Schaldach et al. | |
| 5,411,531 A | 5/1995 | Hill et al. | |
| 5,411,540 A | 5/1995 | Edell et al. | |
| 5,423,872 A | 6/1995 | Cigaina | |
| 5,507,784 A | 4/1996 | Hill et al. | |
| 5,522,862 A | 6/1996 | Testerman et al. | |
| 5,522,865 A | 6/1996 | Schulman et al. | |
| 5,531,778 A | 7/1996 | Maschino et al. | 607/118 |
| 5,540,730 A | 7/1996 | Terry, Jr. et al. | |
| 5,540,734 A | 7/1996 | Zabara | |
| 5,571,150 A | 11/1996 | Wernicke et al. | |
| 5,601,617 A | 2/1997 | Loeb et al. | |
| 5,611,350 A | 3/1997 | John | |
| 5,645,570 A | 7/1997 | Corbucci | |
| 5,651,378 A | 7/1997 | Matheny et al. | |
| 5,658,318 A | 8/1997 | Stroetmann et al. | |
| 5,690,681 A | 11/1997 | Geddes et al. | |
| 5,690,688 A | 11/1997 | Noren et al. | |
| 5,690,691 A | 11/1997 | Chen et al. | |
| 5,700,282 A | 12/1997 | Zabara | |
| 5,702,428 A | 12/1997 | Tippey et al. | |
| 5,702,429 A | 12/1997 | King | |
| 5,707,400 A | 1/1998 | Terry, Jr. et al. | |
| 5,755,750 A | 5/1998 | Petruska et al. | |
| 5,792,212 A | 8/1998 | Weijand | |
| 5,800,474 A | 9/1998 | Benabid et al. | |
| 5,814,092 A | 9/1998 | King | |
| 5,836,994 A | 11/1998 | Bourgeois | |
| 5,861,014 A | 1/1999 | Familoni | |
| 5,913,882 A | 6/1999 | King | |
| 5,916,239 A | 6/1999 | Geddes et al. | |
| 5,928,272 A | 7/1999 | Adkins et al. | |
| 5,941,906 A | 8/1999 | Barreras, Sr. et al. | |
| 5,995,868 A | 11/1999 | Osorio et al. | |
| 6,002,966 A | 12/1999 | Loeb et al. | |
| 6,016,449 A | 1/2000 | Fischell et al. | |
| 6,041,258 A | 3/2000 | Cigaina et al. | |
| 6,083,249 A | 7/2000 | Familoni | |
| 6,101,412 A | 8/2000 | Duhaylongsod | |
| 6,104,955 A | 8/2000 | Bourgeois | |
| 6,104,956 A | 8/2000 | Naritoku et al. | |
| 6,115,628 A | 9/2000 | Stadler et al. | |
| 6,132,361 A | 10/2000 | Epstein et al. | |
| 6,141,590 A | 10/2000 | Renirie et al. | |
| 6,161,044 A | 12/2000 | Silverstone | |
| 6,167,311 A | 12/2000 | Rezai | |
| 6,175,764 B1 | 1/2001 | Loeb et al. | |
| 6,188,929 B1 | 2/2001 | Giordano | |
| 6,219,580 B1 | 4/2001 | Faltys et al. | |
| 6,221,908 B1 | 4/2001 | Kilgard et al. | |
| 6,238,423 B1 | 5/2001 | Bardy | |
| 6,249,704 B1 | 6/2001 | Maltan et al. | |
| 6,253,109 B1 | 6/2001 | Gielen | |
| 6,266,564 B1 | 7/2001 | Hill et al. | |
| 6,269,270 B1 | 7/2001 | Boveja | |
| 6,295,472 B1 | 9/2001 | Rubinstein et al. | |
| 6,304,775 B1 | 10/2001 | Iasemidis et al. | |
| 6,308,102 B1 | 10/2001 | Sieracki | |
| 6,324,421 B1 | 11/2001 | Stadler et al. | |
| 6,327,503 B1 | 12/2001 | Familoni | |
| 6,339,725 B1 | 1/2002 | Naritoku et al. | |
| 6,341,236 B1 | 1/2002 | Osorio et al. | |
| 6,353,762 B1 | 3/2002 | Baudino et al. | |
| 6,356,788 B2 | 3/2002 | Boveja | |
| 6,358,203 B2 | 3/2002 | Bardy | |
| 6,366,813 B1 | 4/2002 | DiLorenzo | |
| 6,366,814 B1 | 4/2002 | Boveja | |
| 6,374,140 B1 | 4/2002 | Rise | |
| 6,381,493 B1 | 4/2002 | Stadler et al. | |
| 6,381,496 B1 * | 4/2002 | Meadows et al. | 607/59 |
| 6,381,499 B1 | 4/2002 | Taylor et al. | |
| 6,418,344 B1 | 7/2002 | Rezai et al. | |
| 6,425,852 B1 | 7/2002 | Epstein et al. | |
| 6,438,423 B1 | 8/2002 | Rezai et al. | |
| 6,449,512 B1 | 9/2002 | Boveja | |
| 6,453,199 B1 | 9/2002 | Kobozev | |
| 6,459,936 B2 | 10/2002 | Fischell et al. | |
| 6,463,328 B1 | 10/2002 | John | |
| 6,466,822 B1 | 10/2002 | Pless | |
| 6,473,639 B1 | 10/2002 | Fischell et al. | |
| 6,473,644 B1 | 10/2002 | Terry, Jr. et al. | |
| 6,477,417 B1 | 11/2002 | Levine | |
| 6,477,418 B2 | 11/2002 | Plicchi et al. | |
| 6,480,743 B1 | 11/2002 | Kirkpatrick et al. | |
| 6,484,132 B1 | 11/2002 | Hively et al. | |
| 6,487,446 B1 | 11/2002 | Hill et al. | |
| 6,505,074 B2 | 1/2003 | Boveja et al. | |
| 6,522,928 B2 | 2/2003 | Whitehurst et al. | |
| 6,532,388 B1 | 3/2003 | Hill et al. | |
| 6,549,804 B1 | 4/2003 | Osorio et al. | |
| 6,556,868 B2 | 4/2003 | Naritoku et al. | |
| 6,564,102 B1 | 5/2003 | Boveja | |
| 6,565,503 B2 | 5/2003 | Leysieffer et al. | |
| 6,579,280 B1 | 6/2003 | Kovach et al. | |
| 6,587,719 B1 | 7/2003 | Barrett et al. | |
| 6,587,724 B2 | 7/2003 | Mann | |
| 6,587,726 B2 | 7/2003 | Lurie et al. | |
| 6,587,727 B2 | 7/2003 | Osorio et al. | |
| 6,591,138 B1 | 7/2003 | Fischell et al. | |
| 6,594,524 B2 | 7/2003 | Esteller et al. | |
| 6,600,953 B2 | 7/2003 | Flesler et al. | |
| 6,609,025 B2 | 8/2003 | Barrett et al. | |
| 6,609,030 B1 | 8/2003 | Rezai et al. | |
| 6,609,031 B1 | 8/2003 | Law et al. | |
| 6,610,713 B2 | 8/2003 | Tracey | |
| 6,611,715 B1 | 8/2003 | Boveja | |
| 6,612,983 B1 | 9/2003 | Marchal | |
| 6,615,081 B1 | 9/2003 | Boveja | |
| 6,615,084 B1 | 9/2003 | Cigaina | |
| 6,615,085 B1 | 9/2003 | Boveja | |
| 6,622,038 B2 | 9/2003 | Barrett et al. | |
| 6,622,041 B2 | 9/2003 | Terry, Jr. et al. | |
| 6,622,047 B2 | 9/2003 | Barrett et al. | |
| 6,628,987 B1 | 9/2003 | Hill et al. | |
| 6,656,960 B2 | 12/2003 | Puskas | |
| 6,662,053 B2 | 12/2003 | William | |
| 6,668,191 B1 | 12/2003 | Boveja | |
| 6,671,547 B2 | 12/2003 | Lyster et al. | |
| 6,671,555 B2 | 12/2003 | Gielen et al. | |
| 6,671,556 B2 | 12/2003 | Osorio et al. | |
| 6,684,104 B2 | 1/2004 | Gordon et al. | |
| 6,684,105 B2 | 1/2004 | Cohen et al. | |
| 6,690,973 B2 | 2/2004 | Hill et al. | |
| 6,690,974 B2 | 2/2004 | Archer et al. | |
| 6,708,064 B2 | 3/2004 | Rezai | |
| 6,721,603 B2 | 4/2004 | Zabara et al. | |
| 6,731,979 B2 | 5/2004 | MacDonald | |
| 6,731,986 B2 | 5/2004 | Mann | |
| 6,754,536 B2 | 6/2004 | Swoyer et al. | |

| | | |
|---|---|---|
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,793,670 B2 | 9/2004 | Osorio et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Sypulkowski |
| 7,054,686 B2 | 5/2006 | MacDonald |
| 7,066,910 B2 * | 6/2006 | Bauhahn et al. ............ 604/151 |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,216,000 B2 * | 5/2007 | Sieracki et al. ............ 607/46 |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,266,412 B2 * | 9/2007 | Stypulkowski ............ 607/48 |
| 7,340,302 B1 | 3/2008 | Falkenberg et al. |
| 2001/0034541 A1 | 10/2001 | Lyden |
| 2001/0037220 A1 | 11/2001 | Merry et al. |
| 2002/0013612 A1 * | 1/2002 | Whitehurst ............ 607/45 |
| 2002/0052539 A1 | 5/2002 | Haller et al. |
| 2002/0065509 A1 | 5/2002 | Lebel et al. |
| 2002/0072782 A1 | 6/2002 | Osorio et al. |
| 2002/0082480 A1 | 6/2002 | Riff et al. |
| 2002/0099412 A1 | 7/2002 | Fischell et al. |
| 2002/0099417 A1 | 7/2002 | Naritoku et al. |
| 2002/0116030 A1 | 8/2002 | Rezai |
| 2002/0120310 A1 | 8/2002 | Linden et al. |
| 2002/0133204 A1 | 9/2002 | Hrdlicka |
| 2002/0143368 A1 | 10/2002 | Bakels et al. |
| 2002/0151939 A1 | 10/2002 | Rezai |
| 2002/0153901 A1 | 10/2002 | Davis et al. |
| 2002/0188214 A1 | 12/2002 | Misczynski et al. |
| 2003/0023282 A1 * | 1/2003 | Barrett et al. ............ 607/45 |
| 2003/0028226 A1 | 2/2003 | Thompson et al. |
| 2003/0055457 A1 | 3/2003 | MacDonald |
| 2003/0074032 A1 | 4/2003 | Gliner |
| 2003/0083716 A1 | 5/2003 | Nicolelis et al. |
| 2003/0088274 A1 | 5/2003 | Gliner et al. |
| 2003/0095648 A1 | 5/2003 | Kaib et al. |
| 2003/0097161 A1 | 5/2003 | Firlik et al. |
| 2003/0109903 A1 | 6/2003 | Berrang et al. |
| 2003/0125786 A1 | 7/2003 | Gliner et al. |
| 2003/0130706 A1 | 7/2003 | Sheffield et al. |
| 2003/0144711 A1 | 7/2003 | Pless et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0181959 A1 | 9/2003 | Dobak |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0036377 A1 | 2/2004 | Mezinis |
| 2004/0039424 A1 | 2/2004 | Merritt et al. |
| 2004/0088024 A1 | 5/2004 | Firlik et al. |
| 2004/0111139 A1 | 6/2004 | McCreery |
| 2004/0112894 A1 | 6/2004 | Varma |
| 2004/0122484 A1 | 6/2004 | Hatlestad et al. |
| 2004/0122485 A1 | 6/2004 | Stahmann et al. |
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199212 A1 | 10/2004 | Fischell et al. |
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0249416 A1 | 12/2004 | Yun et al. |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai et al. |
| 2005/0015128 A1 | 1/2005 | Rezai et al. |
| 2005/0016657 A1 | 1/2005 | Bluger |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathur |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai |
| 2005/0107858 A1 | 5/2005 | Bluger |
| 2005/0113705 A1 | 5/2005 | Fischell et al. |
| 2005/0113744 A1 | 5/2005 | Donoghue et al. |
| 2005/0119703 A1 | 6/2005 | DiLorenzo |
| 2005/0124901 A1 | 6/2005 | Misczynski et al. |

| | | | | | |
|---|---|---|---|---|---|
| 2005/0131467 A1 | 6/2005 | Boveja et al. | 2006/0195163 A1 | 8/2006 | KenKnight et al. |
| 2005/0131485 A1 | 6/2005 | Knudson et al. | 2006/0200206 A1 | 9/2006 | Firlik et al. |
| 2005/0131486 A1 | 6/2005 | Boveja et al. | 2006/0212091 A1 | 9/2006 | Lozano et al. |
| 2005/0131493 A1 | 6/2005 | Boveja et al. | 2006/0217780 A1 | 9/2006 | Gliner et al. |
| 2005/0131506 A1 | 6/2005 | Rezai et al. | 2006/0220839 A1 | 10/2006 | Fifolt et al. |
| 2005/0137480 A1 | 6/2005 | Alt et al. | 2006/0224067 A1 | 10/2006 | Giftakis et al. |
| 2005/0143781 A1* | 6/2005 | Carbunaru et al. ............. 607/11 | 2006/0224191 A1 | 10/2006 | DiLorenzo |
| 2005/0143786 A1 | 6/2005 | Boveja et al. | 2006/0241697 A1 | 10/2006 | Libbus et al. |
| 2005/0148893 A1 | 7/2005 | Misczynski et al. | 2006/0241725 A1 | 10/2006 | Libbus et al. |
| 2005/0148894 A1 | 7/2005 | Misczynski et al. | 2006/0253164 A1 | 11/2006 | Zhang et al. |
| 2005/0148895 A1 | 7/2005 | Misczynski et al. | 2006/0253168 A1 | 11/2006 | Wyler et al. |
| 2005/0153885 A1 | 7/2005 | Yun et al. | 2006/0253169 A1 | 11/2006 | Wyler et al. |
| 2005/0154425 A1 | 7/2005 | Boveja et al. | 2006/0253170 A1 | 11/2006 | Wyler et al. |
| 2005/0154435 A1 | 7/2005 | Stern et al. | 2006/0253171 A1 | 11/2006 | Wyler et al. |
| 2005/0159789 A1 | 7/2005 | Brockway et al. | 2006/0259095 A1 | 11/2006 | Wyler et al. |
| 2005/0161052 A1 | 7/2005 | Rezai et al. | 2006/0264730 A1 | 11/2006 | Stivoric et al. |
| 2005/0165458 A1 | 7/2005 | Boveja et al. | 2006/0265018 A1 | 11/2006 | Smith et al. |
| 2005/0177192 A1 | 8/2005 | Rezai et al. | 2006/0271409 A1 | 11/2006 | Rosenfeld et al. |
| 2005/0177200 A1 | 8/2005 | George et al. | 2006/0293720 A1 | 12/2006 | DiLorenzo |
| 2005/0177206 A1 | 8/2005 | North et al. | 2007/0027486 A1 | 2/2007 | Armstrong et al. |
| 2005/0182389 A1 | 8/2005 | LaPorte et al. | 2007/0032734 A1 | 2/2007 | Najafi et al. |
| 2005/0187590 A1 | 8/2005 | Boveja et al. | 2007/0032834 A1 | 2/2007 | Gliner et al. |
| 2005/0187593 A1 | 8/2005 | Housworth et al. | 2007/0038262 A1 | 2/2007 | Kieval et al. |
| 2005/0187796 A1 | 8/2005 | Rosenfeld et al. | 2007/0043392 A1 | 2/2007 | Gliner et al. |
| 2005/0192644 A1 | 9/2005 | Boveja et al. | 2007/0055320 A1 | 3/2007 | Weinand et al. |
| 2005/0197590 A1 | 9/2005 | Osorio et al. | 2007/0073150 A1 | 3/2007 | Gopalsami et al. |
| 2005/0222631 A1 | 10/2005 | Dalal et al. | 2007/0073346 A1 | 3/2007 | Corbucci et al. |
| 2005/0228693 A1 | 10/2005 | Webb et al. | 2007/0073355 A1 | 3/2007 | DiLorenzo |
| 2005/0240246 A1 | 10/2005 | Lee et al. | 2007/0078491 A1 | 4/2007 | Siejko et al. |
| 2005/0245944 A1 | 11/2005 | Rezai | 2007/0088403 A1 | 4/2007 | Wyler et al. |
| 2005/0245971 A1 | 11/2005 | Brockway et al. | 2007/0088404 A1 | 4/2007 | Wyler et al. |
| 2005/0245990 A1 | 11/2005 | Roberson | 2007/0088405 A1 | 4/2007 | Jacobson et al. |
| 2005/0261542 A1 | 11/2005 | Riehl | 2007/0100278 A1 | 5/2007 | Frei et al. |
| 2005/0267550 A1 | 12/2005 | Hess et al. | 2007/0100397 A1 | 5/2007 | Seeberger et al. |
| 2005/0272280 A1 | 12/2005 | Osypka | 2007/0100398 A1 | 5/2007 | Sloan |
| 2005/0277872 A1 | 12/2005 | Colby, Jr. et al. | 2007/0112393 A1 | 5/2007 | Gliner |
| 2005/0277998 A1 | 12/2005 | Tracey et al. | 2007/0123946 A1 | 5/2007 | Masoud |
| 2005/0283200 A1 | 12/2005 | Rezai et al. | 2007/0135855 A1 | 6/2007 | Foshee et al. |
| 2005/0283201 A1 | 12/2005 | Machado et al. | 2007/0142862 A1 | 6/2007 | Dilorenzo |
| 2005/0283208 A1 | 12/2005 | Von Arx et al. | 2007/0142873 A1 | 6/2007 | Esteller et al. |
| 2005/0288600 A1 | 12/2005 | Zhang et al. | 2007/0149952 A1 | 6/2007 | Bland et al. |
| 2005/0288736 A1 | 12/2005 | Persen et al. | 2007/0150011 A1 | 6/2007 | Meyer et al. |
| 2005/0288760 A1 | 12/2005 | Machado et al. | 2007/0150014 A1 | 6/2007 | Kramer et al. |
| 2006/0009815 A1 | 1/2006 | Boveja | 2007/0150024 A1 | 6/2007 | Leyde et al. |
| 2006/0020292 A1 | 1/2006 | Goetz et al. | 2007/0150025 A1 | 6/2007 | Dilorenzo et al. |
| 2006/0020491 A1 | 1/2006 | Mongeon et al. | 2007/0156179 A1 | 7/2007 | Karashurov |
| 2006/0041222 A1 | 2/2006 | Dewing et al. | 2007/0156450 A1 | 7/2007 | Roehm et al. |
| 2006/0041223 A1 | 2/2006 | Dewing et al. | 2007/0156626 A1 | 7/2007 | Roehm et al. |
| 2006/0041287 A1 | 2/2006 | Dewing et al. | 2007/0161919 A1 | 7/2007 | DiLorenzo |
| 2006/0047205 A1 | 3/2006 | Ludomirsky et al. | 2007/0162086 A1 | 7/2007 | DiLorenzo |
| 2006/0052843 A1 | 3/2006 | Elsner et al. | 2007/0167991 A1 | 7/2007 | DiLorenzo |
| 2006/0058597 A1 | 3/2006 | Machado et al. | 2007/0173901 A1 | 7/2007 | Reeve |
| 2006/0064133 A1 | 3/2006 | Von Arx et al. | 2007/0179534 A1 | 8/2007 | Firlik et al. |
| 2006/0064134 A1 | 3/2006 | Mazar et al. | 2007/0179558 A1 | 8/2007 | Gliner et al. |
| 2006/0064143 A1 | 3/2006 | Von Arx et al. | 2007/0179584 A1 | 8/2007 | Gliner |
| 2006/0069322 A1 | 3/2006 | Zhang et al. | 2007/0203548 A1 | 8/2007 | Pawelzik et al. |
| 2006/0074450 A1 | 4/2006 | Boveja | 2007/0208212 A1 | 9/2007 | DiLorenzo |
| 2006/0079936 A1 | 4/2006 | Boveja | 2007/0208390 A1 | 9/2007 | Von Arx et al. |
| 2006/0079942 A1 | 4/2006 | Deno et al. | 2007/0213785 A1 | 9/2007 | Osorio et al. |
| 2006/0079945 A1 | 4/2006 | Libbus | 2007/0233192 A1 | 10/2007 | Craig |
| 2006/0085046 A1 | 4/2006 | Rezai et al. | 2007/0233193 A1* | 10/2007 | Craig ................ 607/2 |
| 2006/0094971 A1 | 5/2006 | Drew | 2007/0238939 A1 | 10/2007 | Giftakis et al. |
| 2006/0095081 A1 | 5/2006 | Zhou et al. | 2007/0239210 A1 | 10/2007 | Libbus et al. |
| 2006/0100667 A1 | 5/2006 | Machado et al. | 2007/0239211 A1 | 10/2007 | Lorincz et al. |
| 2006/0106430 A1 | 5/2006 | Fowler et al. | 2007/0239220 A1 | 10/2007 | Greenhut et al. |
| 2006/0106431 A1 | 5/2006 | Wyler et al. | 2007/0244407 A1 | 10/2007 | Osorio |
| 2006/0111644 A1 | 5/2006 | Guttag et al. | 2007/0249953 A1 | 10/2007 | Frei et al. |
| 2006/0122525 A1 | 6/2006 | Shusterman | 2007/0249954 A1 | 10/2007 | Virag et al. |
| 2006/0122667 A1 | 6/2006 | Chavan et al. | 2007/0250130 A1 | 10/2007 | Ball et al. |
| 2006/0122864 A1 | 6/2006 | Gottesman et al. | 2007/0250145 A1 | 10/2007 | Kraus et al. |
| 2006/0135877 A1 | 6/2006 | Giftakis et al. | 2007/0255147 A1 | 11/2007 | Drew et al. |
| 2006/0135881 A1 | 6/2006 | Giftakis et al. | 2007/0255155 A1 | 11/2007 | Drew et al. |
| 2006/0155495 A1 | 7/2006 | Osorio et al. | 2007/0255330 A1 | 11/2007 | Lee et al. |
| 2006/0161459 A9 | 7/2006 | Rosenfeld et al. | 2007/0255337 A1 | 11/2007 | Lu |
| 2006/0167497 A1 | 7/2006 | Armstrong et al. | 2007/0255339 A1* | 11/2007 | Torgerson ................ 607/45 |
| 2006/0173493 A1 | 8/2006 | Armstrong et al. | 2007/0260147 A1 | 11/2007 | Giftakis et al. |
| 2006/0173522 A1 | 8/2006 | Osorio | 2007/0260289 A1 | 11/2007 | Giftakis et al. |
| 2006/0190056 A1 | 8/2006 | Fowler et al. | 2007/0265489 A1 | 11/2007 | Fowler et al. |
| 2006/0195155 A1 | 8/2006 | Firlik et al. | 2007/0265508 A1 | 11/2007 | Sheikhzadeh-Nadjar et al. |

| | | |
|---|---|---|
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | DiLorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard, III |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0039895 A1 | 2/2008 | Fowler et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw et al. |
| 2008/0255582 A1 | 10/2008 | Harris |
| 2009/0054795 A1 | 2/2009 | Misczynski et al. |
| 2009/0076567 A1 | 3/2009 | Fowler et al. |

FOREIGN PATENT DOCUMENTS

| | | |
|---|---|---|
| EP | 0402683 | 12/1990 |
| EP | 0713714 | 5/1996 |
| EP | 1139861 | 12/1999 |
| EP | 1070518 | 1/2001 |
| EP | 0944411 | 4/2001 |
| EP | 1145736 A2 | 10/2001 |
| EP | 1483020 | 12/2004 |
| EP | 1486232 | 12/2004 |
| EP | 1595497 | 11/2005 |
| EP | 1120130 | 12/2005 |
| EP | 1647300 | 4/2006 |
| EP | 1202775 | 9/2006 |
| GB | 2026870 | 2/1980 |
| GB | 2079610 | 1/1982 |
| WO | 9302744 | 2/1993 |
| WO | 9417771 | 8/1994 |
| WO | 0064336 A1 | 11/2000 |
| WO | 0108749 | 2/2001 |
| WO | 0064336 A9 | 6/2002 |
| WO | 03085546 | 10/2003 |
| WO | 2004036377 | 4/2004 |
| WO | 2004064918 | 8/2004 |
| WO | 2004069330 | 8/2004 |
| WO | 2004071575 | 8/2004 |
| WO | 2004075982 | 9/2004 |
| WO | 2004112894 | 12/2004 |
| WO | 2005007120 | 1/2005 |
| WO | 2005007232 | 1/2005 |
| WO | 2005028026 A1 | 3/2005 |
| WO | 2005053788 | 6/2005 |
| WO | 2005067599 | 7/2005 |
| WO | 2005101282 | 10/2005 |
| WO | 2006014760 | 2/2006 |
| WO | 2006019822 | 2/2006 |
| WO | 2006050144 | 5/2006 |
| WO | 2006122148 | 11/2006 |
| WO | 2007066343 A2 | 6/2007 |
| WO | 2007072425 | 6/2007 |
| WO | 2007124126 | 11/2007 |
| WO | 2007124190 | 11/2007 |
| WO | 2007124192 | 11/2007 |
| WO | 2007142523 | 12/2007 |

OTHER PUBLICATIONS

Bohning, D.E., et al.; "Feasibility of Vagus Nerve Stimulation—Synchronized Blood Oxygenation Level-Dependent Functional MRI;" A Journal of Clinical and Laboratory Research: Investigative Radiology, vol. 36, No. 8 (Aug. 2001); pp. 470-479.

Boon, Paul, et al.; "Programmed and Magnet-Induced Vagus Nerve Stimulation for Refractory Epilepsy," Journal of Clinical Neurophysiology vol. 18 No. 5; (2001); pp. 402-407.

Clark, K.B., et al.; "Posttraining Electrical Stimulation of Vagal Afferents with Concomitant Vagal Efferent Inactivation Enhances Memory Storage Processes in the Rat;" Neurobiology of Learning and Memory, vol. 70, 364-373 (1998) Art. No. NL983863.

Clark, K.B., et al.; "Enhanced Recognition Memory Following Vagus Nerve Stimulation in Human Subjects," Nature Neuroscience, vol. 2, No. 1, (Jan. 1999) pp. 93-98.

Craig, A.D. (BUD); "Distribution of Trigeminothalamic and Spinothalamic Lamina I Terminations in the Macaque Monkey," The Journal of Comparative Neurology, vol. 477, pp. 119-148 (2004).

DeGiorgo, Christopher M., et al.; "Vagus Nerve Stimulation: Analysis of Device Parameters in 154 Patients During the Long-Term XE5 Study," Epilepsia, vol. 42, No. 8; pp. 1017-1020 (2001).

Devous, Michael D., et al.; "Effects of Vagus Nerve Stimulation on Regional Cerebral Blood Flow in Treatment-Resistant Depression;" National Institute of Mental Health—42nd Annual NCDEU Meeting: Poster Session II; Poster Abstracts, Jun. 10-13, 2002, 1 page; http://www.nimh.nih.gov/ncdeu/abstracts2001/ncdeu2019.cfm.

Hallowitz, R.A., et al.; "Effects Of Vagal Tolleys On Units Of Intralaminar and Juxtalaminar Thalamic Nuclei in Monkeys;" Brain Research, vol. 130 (1977), pp. 271-286.

Harry, J.D., et al.; "Balancing Act: Noise is the Key to Restoring the Body's Sense of Equilibrium," IEEE Spectrum (Apr. 2005)pp. 37-41.

Henry, T.R., et al.; "Brain Blood-Flow Alterations Induced by Therapeutic Vagus Nerve Stimulation in Partial Epilepsy: I. Acute Effects at High and Low Levels of Stimulation;" Epilepsia vol. 39, No. 9; pp. 984-990 (1998).

Henry, MD, T.R.; "Therapeutic Mechanisms of Vagus Nerve Stimulation" Neurology, vol. 59 Suppl. 4 (Sep. 2002); pp. S3-S14.

King, M.D., "Effects of Short-Term Vagus Nerve Stimulation (VNS) on FOS Expression in Rat Brain Nuclei" 58th Annual Scientific Convention of the Society of Biological Psychiatry, (May 2003).

Klapper, M.D., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).

Koo, B., "EEG Changes With Vagus Nerve Stimulation" Journal of Clinical Neurophysiology, vol. 18 No. 5 (Sep. 2001); pp. 434-441.

Labar, D., "Vagus Nerve Stimulation for 1 Year in 269 patients on Unchanged Antiepilectic Drugs" Seizure vol. 13, (2004) pp. 392-398.

Lockard et al., "Feasibility And Safety Of Vagal Stimulation In Monkey Model," Epilepsia, vol. 31 (Supp. 2) (1990), pp. S20-S26.

Liebman, K.M. et al.; "Improvement in Cognitive Function After Vagal Nerve Stimulator Implantation," Epilepsia, vol. 39, Suppl. 6 (1998) 1 page.

Malow, B.A., et al.; "Vagus Nerve Stimulation Reduces Daytime Sleepiness in Epilepsy Patients" NEUROLOGY 57 (2001) pp. 879-884.

McClintock, P., Can Noise Actually Boost Brain Power Physics World Jul. 2002; pp. 20-21.

Mori, T., et al.; "Noise-Induced Entrainment and Stochastic Resonance in Human Brain Waves" Physical Review Letters vol. 88, No. 21 (2002); pp. 218101-1-218101-4.

Rugg-Gunn, F.J., et al.; "Cardiac Arrhythmias in Focal Epilepsy: a Prospective Long-Term Study" www.thelancet.com vol. 364 (2004) pp. 2212-2219.

Rutecki, P.; "Anatomical, Physiological, and Theoretical Basis for the Antiepileptic Effect of Vagus Nerve Stimulation" Epilepsia, vol. 31 Suppl. 2; S1-S6 (1990).

Sahin, M.; et al.; "Improved Nerve Cuff Electrode Recordings with Subthreshold Anodic Currents," IEEE Transactions on Biomedical Engineering, vol. 45, No. 8 (Aug. 1998) pp. 1044-1050.

Schachter, S.C., et al.; "Progress in Epilepsy Research: Vagus Nerve Stimulation," Epilepsia, vol. 39, No. 7 (1998) pp. 677-686.

Tatum, W.O., et al.; "Ventricular Asystole During Vagus Nerve Stimulation for Epilepsy in Humans" American Academy of Neurologgy (1999) p. 1267 (See also pp. 1117, 1166, and 1265).

Tatum, W.O., et al.; "Vagus Nerve Stimulation and Drug Reduction" Neurology, vol. 56, No. 4 (Feb. 2001) pp. 561-563.

Terry et al.; "The Implantable Neurocybernetic Prosthesis System", Pacing and Clinical Electrophysiology, vol. 14, No. 1 (Jan. 1991), pp. 86-93.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Valdez-Cruz, A., et al.; "Chronic Stimulation of the Cat Vagus Nerve Effect on Sleep and Behavior" Progress in Neuro-Psychopharmacology & Biological Psychiatry, vol. 26 (2002) pp. 113-118.

Vonck, K., et al. "The Mechanism of Action Of Vagus Nerve Stimulation for Refractory Epilepsy—The Current Status", Journal of Neurophysiology, vol. 18 No. 5 (2001), pp. 394-401.

Ward, H., M.D., et al.; "Treatment-Refractory Obsessive-Compulsive Disorder: Potential Benefit of VNS Therapy" 23rd Annual Conference of the Anxiety Disorders Association of America (2007).

Woodbury, et al., "Vagal Stimulation Reduces the Severity Of Maximal Electroshock Seizures in Intact Rats. Use of a Cuff Electrode for Stimulating and Recording"; Pacing and Clinical Electrophysiology, vol. 14 (Jan. 1991), pp. 94-107.

Zabara, J. "Inhibition of Experimental Seizures in Canines by Repetivie Vagal Stimulation" Epilepsia vol. 33, No. 6 (1992); pp. 1005-1012.

Dodrill, Ph.D., et al.; "Effects of Vagal Nerve Stimulation on Cognition and Quality of Life in Epilepsy," Epilepsy and Behavior, vol. 2 (2001); pp. 46-53.

Fromes, G. A.et al.; "Clinical Utility of On-Demand Magnet use with Vagus Nerve Stimulation," AES Proceedings, p. 117.

George, M.S., et al.; "Open Trial of VNS Therapy in Severe Anxiety Disorders," 156th American Psychiatric Association Annual Meeting; May 17-22, 2003.

George, M.S., et al.; "Vagus Nerve Stimulation: A New Tool for Brain Research and Therapy," Society of Biological Psychiatry vol. 47 (2000) pp. 287-295.

Fanselow, E.E., et al.; "Reduction of Pentylenetetrazole-Induced Seizure Activity in Awake Rates by Seizure Triggered Trigeminal Nerve Stimulation," The Journal of Neuroscience, Nov. 1, 2000; vol. 20/21 ; pp. 8160-8168.

Basser, Peter J., et al.; "New Currents in Electrical Stimulation of Excitable Tissues," Annu. Rev. Biomed. Eng. 2000; 02:377-97.

* cited by examiner

DOSING LIMITATION FOR AN IMPLANTABLE MEDICAL DEVICE

BACKGROUND OF THE INVENTION

1. Field of the Invention

This invention relates generally to medical devices, and, more particularly, to methods, apparatus, and systems for limiting patient-initiated electrical signal therapy by a medical device.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. Nos. 4,702,254, 4,867,164, and 5,025,807 to Dr. Jacob Zabara, which are hereby incorporated in this specification in their entirety by reference.

More generally, the endogenous electrical activity (i.e., activity attributable to the natural functioning of the patient's own body) of a neural structure of a patient may be modulated in a variety of ways. In particular, the electrical activity may be modulated by exogenously applied (i.e., from a source other than the patient's own body) electrical, chemical, or mechanical signals applied to the neural structure. The modulation (hereinafter referred to generally as "neurostimulation" or "neuromodulation") may involve the induction of afferent action potentials, efferent action potentials, or both, in the neural structure, and may also involve blocking or interrupting the transmission of endogenous electrical activity traveling along the nerve. Electrical signal therapy or electrical modulation of a neural structure (also known as "electrical signal therapy") refers to the application of an exogenous therapeutic electrical signal (as opposed to a chemical or mechanical signal), to the neural structure. Electrical signal therapy may be provided by implanting an electrical device underneath the skin of a patient and delivering an electrical signal to a nerve such as a cranial nerve. The electrical signal therapy may involve performing a detection step, with the electrical signal being delivered in response to a detected body parameter. This type of stimulation is generally referred to as "active," "feedback," or "triggered" stimulation. Alternatively, the system may operate without a detection system once the patient has been diagnosed with epilepsy (or another medical condition), and may periodically apply a series of electrical pulses to the nerve (e.g., a cranial nerve such as a vagus nerve) intermittently throughout the day, or over another predetermined time interval. This type of stimulation is generally referred to as "passive," "non-feedback," or "prophylactic," stimulation. The stimulation may be applied by an implantable medical device that is implanted within the patient's body.

Generally, implantable medical devices (IMD) are capable of receiving a signal that may affect the operation of the IMD from an external source, such as a patient-initiated signal or a signal in the patient's environment. For example, a patient-initiated signal may be used to activate a predetermined function of the IMD, such as providing additional therapeutic electrical signals to a cranial nerve of the patient. A magnetic sensor may be provided in the IMD to detect a significant magnetic field, either from the patient or the patient's environment (for example an MRI machine) and in response, the IMD may activate a predetermined function. A patient-initiated signal such as a magnetic field may be an inhibitory input or an excitatory input. The inhibitory input may relate to inhibiting a function normally performed by the IMD. For example, application of a first patient-initiated magnetic field to the IMD may cause delivery of the electrical signal from the IMD to the nerve to be inhibited for a certain time period. Conversely, application of a second patient-initiated magnetic field signal to the IMD may comprise an excitatory input that may prompt the IMD to perform additional functions. For example, additional electrical signal therapy may be performed by the IMD based upon a second patient-initiated magnetic signal input. The magnetic signal input may be generated by a patient by placing a magnet proximate the skin area under which the implantable medical device resides in the human body. Both types of magnetic field signals are typically referred to as "magnet modes" or as "magnet mode" operation. Other types of patient-initiated signals, such as a tap signal on the IMD, or a radio-frequency (RF) signal provided to the device, may be used in addition to magnetic field signals.

One problem associated with the state of the art is that optimal safety and efficacy of neurostimulation by an IMD may be compromised by allowing a patient to initiate neurostimulation ad libitum. For example, excessive delivery of electrical current to a neurological structure may result in a net electrical charge on, and subsequent damage to, the target neurological structure. Current doses that do not lead to tissue damage may lead to discomfort. Also, extra dosing may lead to reduced efficacy by interfering with short-term or long-term recovery periods necessary or advisable for proper and/or safe neural functioning. Further, battery life can be shortened by excessive dosing. On the other hand, blanket prohibition of patient-initiated neurostimulation may lead to ineffective alleviation of symptoms during acute crisis, when extra dosing may be helpful, e.g., during an epileptic seizure suffered by a patient having an implanted vagus nerve stimulation (VNS) device. Also, blanket prohibition of patient-initiated neurostimulation, if communicated to the patient, may remove any placebo effect benefit the patient may receive from signaling the IMD to perform neurostimulation via the actions of passing the magnet over the IMD or tapping the IMD, among other modes of initiating the therapeutic electrical signal.

The present invention is directed to overcoming, or at least reducing, the effects of one or more of the problems set forth above.

SUMMARY OF THE INVENTION

In one aspect, the present invention provides a method for providing an alternative mode of electrical signal therapy provided by an implantable medical device (IMD) to a cranial nerve of a patient, comprising specifying a threshold of an electrical signal parameter; receiving an input from a patient; determining whether to implement the alternative mode based on said input and said threshold, said alternative mode differing in at least one neurostimulation parameter from a normal stimulation mode; and performing the alternative mode of electrical signal therapy, in view of the result of the determining step, or not performing the alternative mode of electrical signal therapy, in view of the result of the determining step.

In one aspect, the present invention provides a method for limiting patient-initiated electrical signal therapy provided by an implantable medical device (IMD) to a cranial nerve of a patient by specifying at least one electrical signal therapy limit selected from the group consisting of a maximum number of patient-initiated signals to provide a therapeutic electrical signal per a time period, a maximum dose of the therapeutic electrical signal per a time period, a maximum duration of the therapeutic electrical signal per a time period, a maximum rate of change of the number of patient-initiated signals to provide a therapeutic electrical signal per a time period, a maximum rate of change of the dose of the therapeutic electrical signal per a time period, and a maximum rate of change of the duration of the electrical signal therapy per a time period; receiving a patient-initiated signal to begin a therapeutic electrical signal; determining whether or not said electrical signal therapy limit is exceeded by said step of detecting a patient-initiated signal; and performing an action in response to said step of determining whether or not said limit is exceeded, said action selected from the group consisting of providing a first electrical signal therapy to said cranial nerve, providing a second, reduced electrical signal therapy to said cranial nerve, providing a third, enhanced electrical signal therapy to said cranial nerve, inhibiting an electrical signal therapy to said cranial nerve, providing a background electrical signal to said cranial nerve, and inhibiting a background electrical signal to said cranial nerve.

In another aspect, the present invention provides a method for limiting patient-initiated electrical signal therapy provided by an implantable medical device (IMD) to a cranial nerve of a patient by specifying at least one limit on patient-initiated electrical signal therapy to a cranial nerve of a patient; receiving a patient-initiated signal to provide an electrical signal therapy to a cranial nerve; determining whether or not said at least one limit on patient-initiated therapy is exceeded by said step of receiving a patient-initiated signal; providing an electrical signal therapy to said cranial nerve of the patient if said at least one limit is not exceeded by said step of receiving a patient-initiated signal; and not providing an electrical signal therapy to said cranial nerve of the patient if said at least one limit is exceeded by said step of receiving a patient-initiated signal.

In another aspect, the present invention provides a method for limiting patient-initiated electrical signal therapy provided by an implantable medical device (IMD) to a cranial nerve of a patient by specifying at least one limit on patient-initiated electrical signal therapy to a cranial nerve of a patient; receiving a patient-initiated signal to provide an electrical signal therapy to a cranial nerve; determining whether or not said at least one limit on patient-initiated therapy is exceeded by said step of receiving a patient-initiated signal; providing a first therapeutic electrical signal to said cranial nerve of the patient if said at least one limit is not exceeded by said step of receiving a patient-initiated signal; and providing a second, reduced therapeutic electrical signal to said cranial nerve of the patient if said at least one limit is exceeded by said step of receiving a patient-initiated signal.

In one aspect, the present invention provides an implantable medical device (IMD) for providing a therapeutic electrical signal to a cranial nerve of a patient's body, including a sensor to detect a patient-initiated signal to initiate an electrical signal therapy; and a controller operatively coupled to said sensor, said controller to determine if said patient-initiated signal to initiate an electrical signal therapy exceeds a predetermined limit on providing a therapeutic electrical signal to a cranial nerve of a patient, provide a therapeutic electrical signal to said cranial nerve if said patient-initiated signal does not exceed said predetermined limit, and not provide a therapeutic electrical signal to said cranial nerve if said patient-initiated signal does exceed said predetermined limit.

BRIEF DESCRIPTION OF THE DRAWINGS

The invention may be understood by reference to the following description taken in conjunction with the accompanying drawings, in which like reference numerals identify like elements, and in which.

Figure 1A:
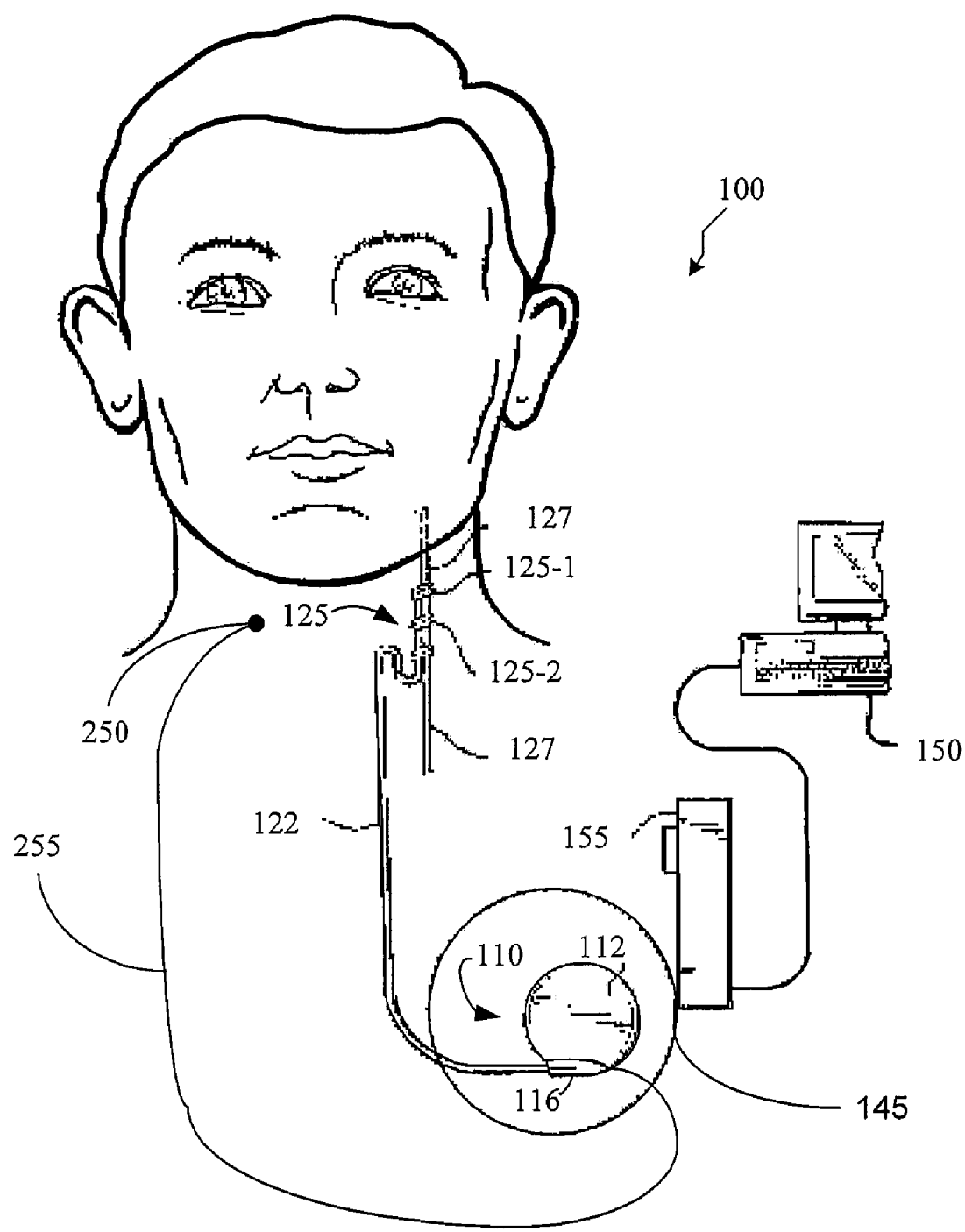
FIGS. 1A-1C provide stylized diagrams of an implantable medical device implanted into a patient's body for providing an electrical signal to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments of the present invention provide for an input to the IMD that would prompt the IMD to operate in an alternative mode for a predetermined time period, or until another triggering input is received. The alternative mode may provide for prompting an alternative operation of the IMD, by which is meant a mode other than a primary mode. A primary mode is a preprogrammed mode in which the IMD operates for a majority of the time and in which the IMD delivers a majority of its electrical signal therapy, as represented as the sum of the delivered doses, to the patient. The alternative mode differs from the primary mode in at least one neurostimulation parameter. Neurostimulation parameters in which the alternative mode can differ from the primary mode will be discussed in more detail below. In one embodiment, the alternative mode is a patient-initiated mode of operation. The alternative mode(s) may provide flexibility in controlling the operation of the IMD.

Although not so limited, a system capable of implementing embodiments of the present invention is described below.

Figure 1B:
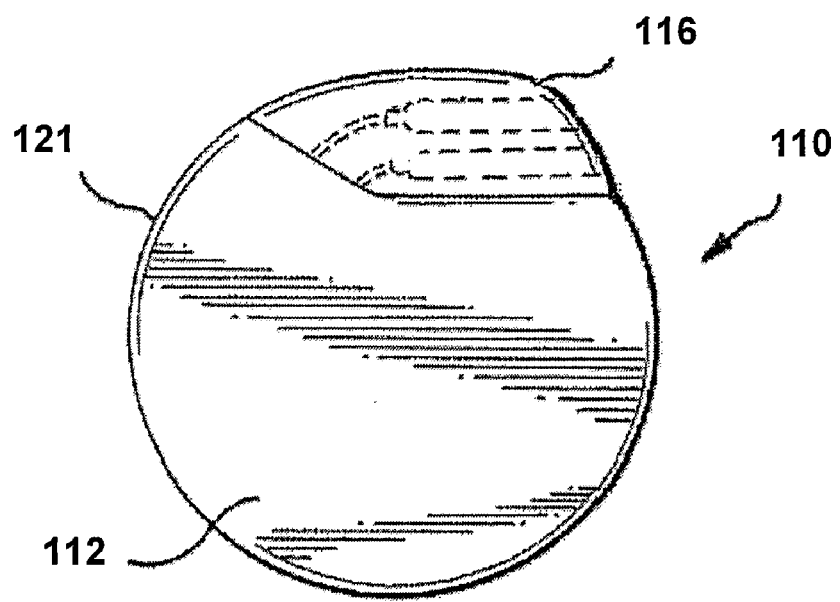
Figure 1C:
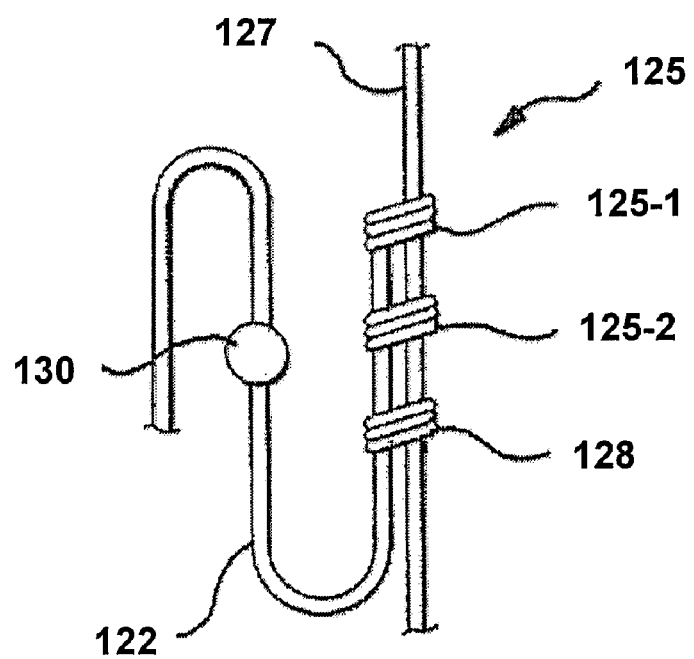

FIGS. 1A-1C depict a stylized implantable medical system 100 for implementing one or more embodiments of the present invention. FIGS. 1A-1C illustrate an electrical signal generator 110 having main body 112 comprising a case or shell 121 (FIG. 1B) with a header 116 (FIG. 1A) for connecting to leads 122. The generator 110 is implanted in the patient's chest in a pocket or cavity formed by the implanting surgeon just below the skin (indicated by a line 145, FIG. 1A), similar to the implantation procedure for a pacemaker pulse generator.

A stimulating nerve electrode assembly 125, preferably comprising an electrode pair, is conductively connected to the distal end of an insulated, electrically conductive lead assembly 122, which preferably comprises a pair of lead wires (one wire for each electrode of an electrode pair). Lead assembly 122 is attached at its proximal end to connectors on the header 116 (FIG. 1B) on case 121. The electrode assembly 125 may be surgically coupled to a cranial nerve 127 in the patient's neck or at another location, e.g., near the patient's diaphragm. Other cranial nerves may also be used to deliver the therapeutic electrical signal. The electrode assembly 125 preferably comprises a bipolar stimulating electrode pair 125-1, 125-2 (FIG. 1C), such as the electrode pair described in U.S. Pat. No. 4,573,481 issued Mar. 4, 1986 to Bullara. Suitable electrode assemblies are available from Cyberonics, Inc., Houston, Tex., USA as the Model 302 electrode assembly. However, persons of skill in the art will appreciate that many electrode designs could be used in the present invention, including unipolar electrodes. Returning to FIGS. 1A and 1C, the two electrodes are preferably wrapped about the cranial nerve 127, and the electrode assembly 125 may be secured to the nerve by a spiral anchoring tether 128 (FIG. 1C) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue (FIG. 1C).

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1C), which may comprise two spiral loops of a three-loop helical assembly. The lead assembly 122 may comprise two distinct lead wires or a coaxial cable whose two conductive elements are respectively coupled to one of the conductive electrode ribbons. One suitable method of coupling the lead wires or cable to the electrodes 125-1, 125-2 comprises a spacer assembly such as that disclosed in U.S. Pat. No. 5,531,778, although other known coupling techniques may be used.

The elastomeric body portion of each loop is preferably composed of silicone rubber, and the third loop 128 (which typically has no electrode) acts as the anchoring tether for the electrode assembly 125.

The electrical pulse generator 110 may be programmed with an external computer 150 using programming software of the type copyrighted by the assignee of the instant application with the Register of Copyrights, Library of Congress, or other suitable software based on the description herein, and a programming wand 155 to facilitate radio frequency (RF) communication between the computer 150 (FIG. 1A) and the pulse generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A variety of stimulation therapies may be provided in implantable medical systems 100 of the present invention. Different types of nerve fibers (e.g., A, B, and C fibers being different fibers targeted for stimulation) respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long term stimulation.

As used herein, the terms "stimulating" and "stimulator" may generally refer to delivery of a signal, stimulus, or impulse to neural tissue for affecting neuronal activity of a neural tissue (e.g., a volume of neural tissue in the brain or a nerve). The effect of such stimulation on neuronal activity is termed "modulation"; however, for simplicity, the terms "stimulating" and "modulating", and variants thereof, are sometimes used interchangeably herein. The effect of delivery of the stimulation signal to the neural tissue may be excitatory or inhibitory and may potentiate acute and/or long-term changes in neuronal activity. For example, the effect of "stimulating" or "modulating" a neural tissue may comprise on one more of the following effects: (a) changes in neural tissue to initiate an action potential (bi-directional or uni-directional); (b) inhibition of conduction of action potentials (endogenous or externally stimulated) or blocking the conduction of action potentials (hyperpolarizing or collision blocking), (c) affecting changes in neurotransmitter/neuromodulator release or uptake, and (d) changes in neuro-plasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization.

In some embodiments, the IMD 200 may perform "background" stimulation according to a preprogrammed normal operation mode. The background stimulation may refer to a second electrical signal that is delivered during a second time period, wherein a normal stimulation mode is implemented in a first time period. Embodiments of the present invention may be employed to provide a second electrical signal at a relatively low level, e.g., at a level that is substantially imperceptible to a patient, during a secondary period that may include a portion of the off-time of the first signal. A second electrical signal provided during an off-time of the first signal may be referred to hereinafter as "background" stimulation or modulation. For example, an IMD 200 may apply a second electrical signal having a reduced frequency, current, or pulse width relative to the first electrical signal during off-time of the first period, in addition to the first electrical signal applied during a primary period. Also, an IMD 200 may apply a third electrical signal having an increased frequency, current, or pulse width relative to the first electrical signal during off-time of the first period. Without being bound by theory, applying a background electrical signal may allow the first electrical signal to be reduced to a level sufficient to reduce one or more side effects without reducing therapeutic efficacy.

In some embodiments of the present invention, the first and second time periods at least partially overlap, and a second electrical stimulation signal may be applied during at least a portion of the first time period. In a more particular embodiment, the second time period only partially overlaps the first, and the second electrical stimulation signal is applied during a portion of the first time period and continues during a period in which the first signal is not applied. This type of stimulation is referred to hereinafter as "overlaid" stimulation or modulation. Overlaid and/or background stimulation embodiments of the invention may increase efficacy of a stimulation therapy, reduce side effects, and/or increase tolerability of the first signal to higher levels of stimulation.

Embodiments of the present invention provide for patient-initiated electrical signal therapy based upon one or more external inputs received by the IMD 200. For example, the IMD 200 may receive various inputs that could prompt a temporary interruption or deviation from normal stimulation operation. For example, a magnet may be placed proximate to the IMD 200, which may be an indication that the patient or a physician desires to alter the normal operation of the IMD 200. The amount of time that the magnet is detected may determine the type of deviation from the normal operation that will occur. Various devices, e.g., a Reed Switch, a Hall Effect sensor, etc., may be employed to detect a magnetic field in order to react to a magnet being placed proximate to the IMD 200. As another example, a tap sensor may be employed to detect a tap applied to the skin over the IMD 200. As a third example, an RF sensor may be employed to detect a radio frequency signal generated proximate to the IMD 200.

Further, an external input received by the IMD 200 may be used to temporarily alter the normal operation of the IMD 200. For example, the patient may desire to temporarily stop any stimulation activity. An input from the patient (e.g., a magnetic input) may be used to suspend stimulation activity. In one embodiment, an input from the patient may prompt the IMD 200 to enter into reduced stimulation mode, wherein a background signal that does not cause certain stimulation side-effects, may be implemented. The amount of time to employ the alternative stimulation mode, as well as the type of alternative stimulation mode, may be pre-programmed into the IMD 200, and may be selected from a plurality of pre-programmed alternative stimulation modes.

Alternatively or in addition, an input from the patient may prompt the IMD 200 to perform a patient-initiated electrical signal therapy regardless of whether such therapy is indicated by normal operation of the IMD 200. However, depending on the patient, his medical condition, and other considerations, it may be desirable that patient-initiated electrical signal therapy be limited in one or more aspects, as will be discussed in more detail below. For example, for some patients, there may be a limitation as to the number of patient-initiated electrical signal therapy operations that may be provided during the alternative stimulation mode.

Figure 2A:
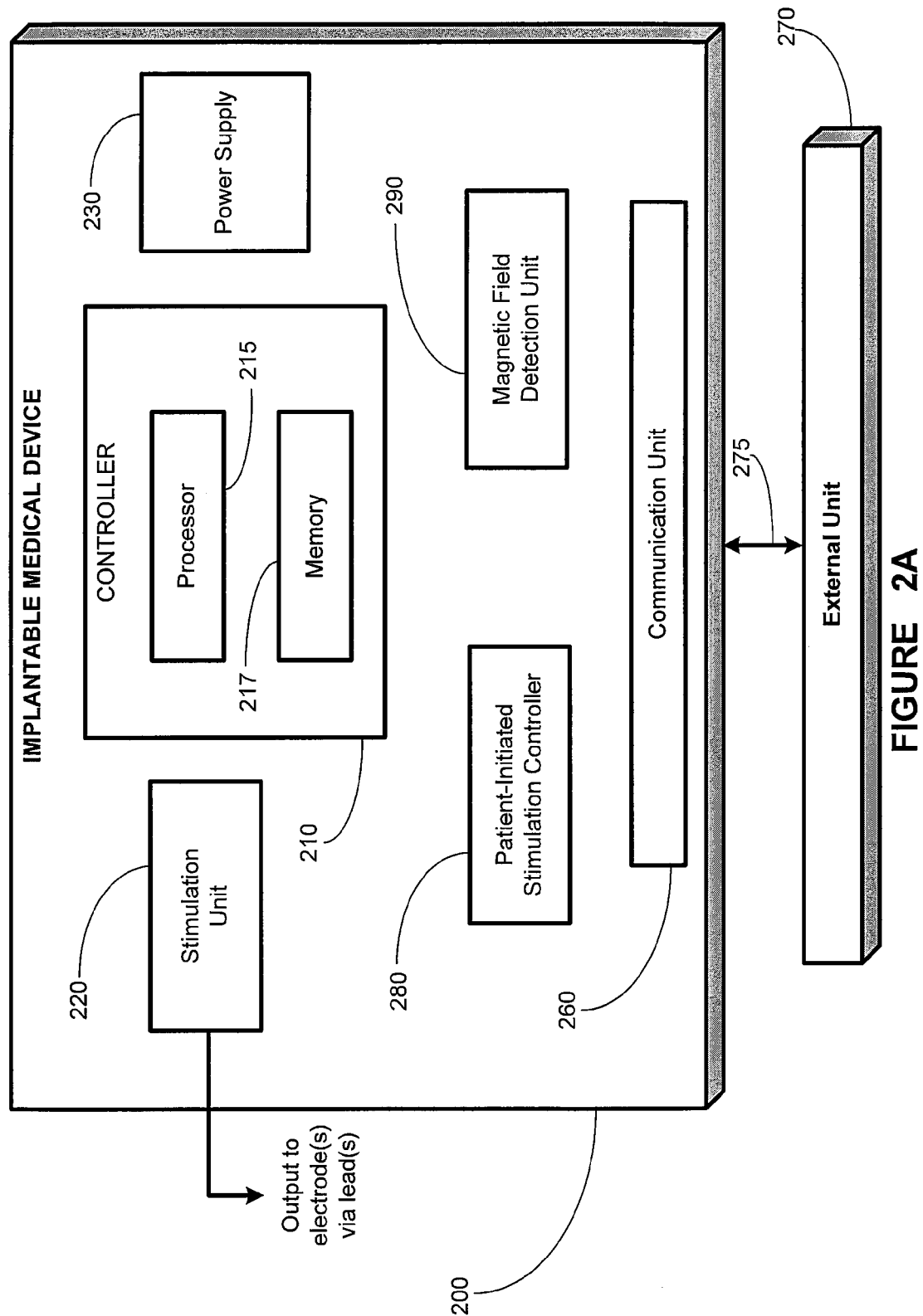
FIG. 2A illustrates a block diagram depiction of the implantable medical device of FIG. 1, in accordance with one illustrative embodiment of the present invention.

Turning now to FIG. 2A, a block diagram depiction of an implantable medical device, in accordance with one illustrative embodiment of the present invention is illustrated. The IMD 200 may be used for stimulation to treat various disorders, including without limitation epilepsy, neuropsychiatric disorders (including but not limited to depression), eating disorders/obesity, traumatic brain injury/coma, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, and reproductive endocrine disorders (including fertility). The IMD 200 may be coupled to various leads, e.g., 122 (FIGS. 1A, 1C). Stimulation signals used for therapy may be transmitted from the IMD 200 to target areas of the patient's body, specifically to various electrodes associated with the leads 122. Stimulation signals from the IMD 200 may be transmitted via the leads 122 to stimulation electrodes (electrodes that apply the therapeutic electrical signal to the target tissue) associated with the electrode assembly 125 (FIG. 1A). Further, signals from sensor electrodes (electrodes that are used to sense one or more body parameters such as temperature, heart rate, brain activity, etc.) may also traverse the leads back to the IMD 200.

The IMD 200 may comprise a controller 210 capable of controlling various aspects of the operation of the IMD 200. The controller 210 is capable of receiving internal data and/or external data and generating and delivering a stimulation signal to target tissues of the patient's body. For example, the controller 210 may receive manual instructions from an operator externally, or may perform stimulation based on internal calculations and programming. The controller 210 is capable of affecting substantially all functions of the IMD 200.

The controller 210 may comprise various components, such as a processor 215, a memory 217, etc. The processor 215 may comprise one or more micro controllers, micro processors, etc., that are capable of executing a variety of software components. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical signal therapy signals to one or more electrodes via leads. The stimulation unit 220 is capable of delivering either a programmed, primary mode electrical signal or a secondary mode, patient-initiated electrical signal to the leads 122 coupled to the IMD 200. The secondary mode, patient initiated signal may be programmed or may determined according to an algorithm in response to a determination of whether a threshold or limit for the electrical signal is exceeded or not exceeded. The electrical signal may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed. The patient-initiated electrical signal therapy can be limited as will be described below.

Figure 2B:
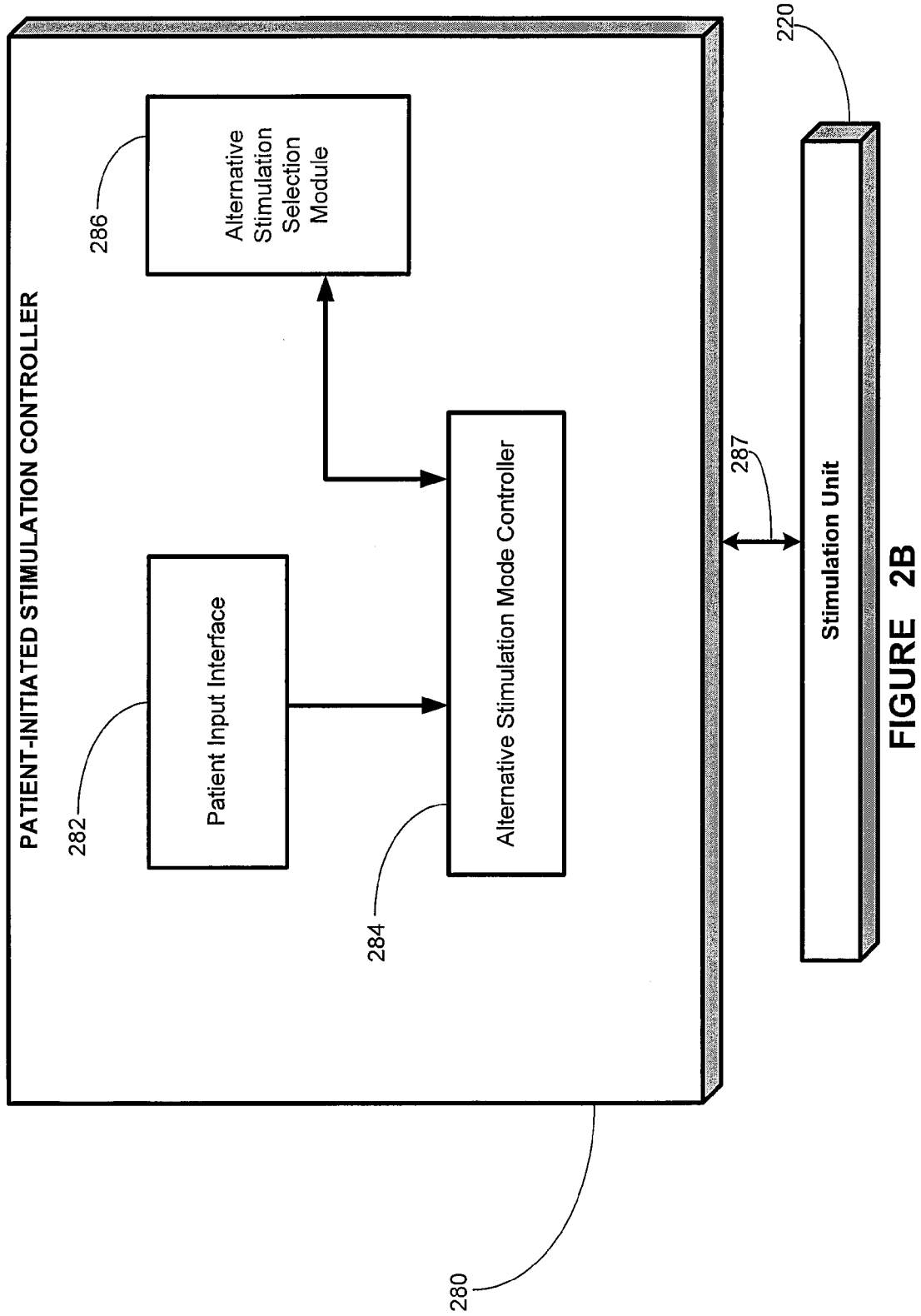
FIG. 2B illustrates a block diagram depiction of the patient-initiated electrical signal controller shown in FIG. 2A.

The IMD 200 may also comprise a patient-initiated stimulation controller 280. The patient-initiated stimulation controller 280 is capable of implementing alternative stimulation modes, such as a patient-initiated electrical signal mode, in response to patient input. The patient-initiated stimulation controller 280 is shown in more detail in FIG. 2B. A patient input interface 282 detects input from the patient, such as that received from the magnetic field detection unit 290 (FIG. 2A), and communicates the detected input to an alternative stimulation mode controller 284. The alternative stimulation mode controller 284 controls alternative stimulation, such as a patient-initiated electrical signal alone or in combination with background stimulation, by taking the input from the patient input interface 282 and communicating with an alternative stimulation selection module 286. The alternative stimulation selection module 286 selects which (if multiple) preprogrammed alternative stimulation modes is to be implemented. The preprogrammed modes may be stored within and retrieved from the memory 217. Once an alternative stimulation mode is selected by the alternative stimulation selection module 286, it communicates with alternative stimulation mode controller 284, which then implements the alternative stimulation mode. The patient-initiated stimulation controller 280 can communicate with the stimulation unit 220 (FIG. 2A) to authorize delivery of a patient-initiated electrical signal via the leads 122 to the electrodes 125 and thence to the cranial nerve 127.

In limiting patient-initiated electrical signal therapy provided by the IMD 200, at least one electrical signal therapy limit is specified. The at least one limit may be selected from the group consisting of a maximum number of patient-initiated signals to provide a therapeutic electrical signal per a time period, a maximum dose of the therapeutic electrical signal per a time period, a maximum duration of the therapeutic electrical signal per a time period, a maximum rate of change of the number of patient-initiated signals to provide a therapeutic electrical signal per a time period, a maximum rate of change of the dose of the therapeutic electrical signal per a time period, and a maximum rate of change of the duration of the electrical signal therapy per a time period. In some embodiments, multiple electrical signal therapy limits may be provided, for example a first limit may comprise 5 patient-initiated signals to provide a therapeutic electrical signal in 24 hours, and a second limit may comprise 8 patient-initiated signals to provide a therapeutic electrical signal in 48 hours. The at least one electrical signal therapy limit can be stored in memory 217.

Specification of the at least one electrical signal therapy limit can be performed prior to implantation of the IMD 200, such as during the manufacturing process or by the implanting physician, either to the physician's default signal therapy limit or to a limit set after consideration of the patient's particular medical condition, among other possible considerations. Alternatively or in addition, specification of the at least one electrical signal therapy limit can be performed after implantation, either to the physician's default limit or to a limit set after consideration of the patient's particular medical condition, his tolerance of the IMD 200, and the efficacy of the IMD 200, among other possible considerations.

Each of the electrical signal therapy limits listed above can be considered over a time period. Any time period can be considered and defined programmably. In one embodiment, at least one said time period begins at implantation of the device. This time period can continue indefinitely, i.e., the time period may comprise the entire operational life of the unit.

In another embodiment, the time period has a duration of from about 10 sec to about 720 hr, such as from about 1 min to about 24 hr, more particularly from about 30 min to about 6 hr. The time period can be continuous, that is, comprising a moving time period representing a length of time ending at the present moment and beginning at a timepoint equal to the defined time period duration before the present moment. For example, an electrical signal limit may comprise a number of patient-initiated signals to provide a therapeutic electrical signal in the previous 24 hours from the present moment. In such embodiments, the system may also define a sampling interval, i.e., may recalculate the moving time period at intervals of from 1 second to one hour, or other time periods such as every 3 hours, every day, or even longer. Different sampling intervals may be used depending upon the time period duration, for example a moving time period of 24 hours need not be updated more frequently than once per hour, as more frequent updating may impose a calculational burden on the IMD that far exceeds any therapeutic benefit. Alternatively, the time period can be externally synchronized, that is, representing a length of time beginning at a particular point in time (such as a particular time of the clock or a particular time after implantation of the IMD 200) and ending at a point in time equal to the time period duration after the beginning of the time period.

The time period can occur once, such as if the time period is the entire operational life of the unit, or it can be repeated on a regular or irregular schedule. For example, the time period can be scheduled to repeat at particular hours of the day. In another embodiment, the time period can be scheduled to commence no earlier than a specified length of time after an immediately prior time period ended.

Multiple time periods, such as two or more time periods, can be considered, wherein the multiple time periods may be consecutive or partially or wholly overlapping. Reference herein to such embodiments may use the terms "first time period," "second time period," etc.

In one embodiment, the electrical signal therapy limit is a maximum number of patient-initiated signals to provide a therapeutic electrical signal per a time period. The number of patient-initiated signals to provide a therapeutic electrical signal can be calculated by incrementing a counter on each patient-initiated signal (magnet swipe, tap, RF communication, or the like) during the time period.

In one embodiment, the electrical signal therapy limit is a maximum dose of neurostimulation charge per a time period. The dose can be calculated by summing the products of the amplitudes and pulse widths of each current pulse during the time period. The maximum dose can be considered for patient-initiated electrical signal therapy only or for both patient-initiated and preprogrammed electrical signal therapy.

In one embodiment, the electrical signal therapy limit is a maximum duration of neurostimulation per a time period. The duration can be calculated by summing the durations of each current pulse during the time period. The maximum duration can be considered for patient-initiated electrical signal therapy only or for both patient-initiated and preprogrammed electrical signal therapy.

In one embodiment, the electrical signal therapy limit is a maximum rate of change of the number of neurostimulation bursts per a time period. The rate of change is defined as the absolute magnitude of the number of bursts in a first subperiod minus the number of bursts in a second subperiod.

In one embodiment, the electrical signal therapy limit is a maximum rate of change of the dose of neurostimulation charge per a time period. The rate of change is defined as the absolute magnitude of the charge dose in a first subperiod minus the charge dose in a second subperiod. The maximum rate of change can be considered for patient-initiated electrical signal therapy only or for both patient-initiated and preprogrammed electrical signal therapy.

In one embodiment, the electrical signal therapy limit is a maximum rate of change of the duration of neurostimulation per a time period. The rate of change is defined as the absolute magnitude of the summed durations of current pulses in a first subperiod minus the summed durations of current pulses in a second subperiod. The maximum rate of change can be considered for patient-initiated electrical signal therapy only or for both patient-initiated and preprogrammed electrical signal therapy.

In one embodiment, a first time period has a duration of about 2 hr and a second time period has a duration of about 4 hr or about 6 hr, wherein the maximum number of patient-initiated signals to provide a therapeutic electrical signal during the second time period is zero.

In one embodiment, a first time period has a duration of about 2 hr and a second time period has a duration of at least about 4 hr or about 6 hr, wherein a first time period begins at the first patient initiation of neurostimulation after the minimum duration of the second time period has occurred and wherein the maximum number of patient-initiated signals to provide a therapeutic electrical signal during the second time period is zero.

Returning to FIG. 2A, at least one of a presence of a magnetic field, a tap input, or a radio frequency (RF) input can be detected by apparatus known in the art, such as those discussed above. The apparatus, for example the magnetic field detection unit 290, or the IMD controller 215 may determine a characteristic of said magnetic field, tap input, or RF input, such as determining at least one of a duration of said magnetic field, a magnitude of said magnetic field, or a number of tap inputs received, among other characteristics.

Based on the at least one electrical signal therapy limit specified above and stored in memory 217, and the receipt of said at least one of said presence of said magnetic field, said tap input, or said RF input, such as a magnetic field detected by magnetic field detection unit 290, whether or not said electrical signal therapy limit is exceeded by said step of detecting a patient-initiated signal is determined. The determination can involve a comparison of the calculated number of patient-initiated signals, the total dose, the total duration, or the rate of change of any of the foregoing with the electrical signal therapy limit in view of the patient-initiated signal, characteristics of the received input, and the various modes of electrical signal therapy with which the unit may be preprogrammed.

In response to said step of determining whether or not said limit is exceeded, an action is performed selected from the group consisting of providing a first electrical signal therapy to said cranial nerve, providing a second, reduced electrical signal therapy to said cranial nerve, providing a third, enhanced electrical signal therapy to said cranial nerve, inhibiting an electrical signal therapy to said cranial nerve, providing a background electrical signal to said cranial nerve, and inhibiting a background electrical signal to said cranial nerve.

In one embodiment, if patient-initiated electrical signal is not permitted (e.g., the maximum number of patient-initiated signals, the total dose, the total duration during the currently elapsing time period is zero, or such limit is greater than zero but has already been reached during the currently elapsing time period), then no electrical signal therapy is performed in response to the received input. In another embodiment, if patient-initiated electrical signal is permitted during the currently elapsing time period, then the electrical signal therapy may follow the first mode of electrical signal therapy, a second mode electrical signal therapy reduced in one or more electrical signal stimulation parameters relative to the first mode (e.g., a mode having a lower pulse amplitude, pulse frequency, burst duration, interburst interval, or two or more thereof, among other electrical signal characteristics) may be applied to the cranial nerve 127, or a third mode electrical signal therapy may be applied that is increased in one or more electrical signal stimulation parameters relative to the first mode (e.g., a mode having a greater pulse amplitude, pulse frequency, burst duration, interburst interval, or two or more thereof, among other electrical signal characteristics). The mode of electrical stimulation can be chosen or modified by the processor 215 and communicated to the stimulation unit 220.

In one embodiment, at least one neurostimulation parameter can be determined by the controller 215 based upon whether or not the electrical signal therapy limit is exceeded or is not exceeded. If the limit is not exceeded, a first electrical signal therapy may be provided to the patient. Providing the first electrical signal therapy may comprise providing a pulsed electrical signal defined by at least one parameter selected from the group consisting of a first current amplitude, a first pulse width, a first frequency, a first on-time, a first off-time, a first number of pulses per burst, a first interburst period, and a first interpulse interval;

If the electrical signal therapy is exceeded, in one embodiment, electrical signal therapy may be inhibited. This may involve completely inhibiting patient-initiated therapy for a predetermined time period, or until it is subsequently determined that the limit is no longer exceeded. In another embodiment, inhibiting the electrical signal therapy may comprise providing a second, reduced electrical signal therapy to the patient, with the reduced electrical signal therapy comprising providing a pulsed electrical signal defined by at least one parameter selected from the group consisting of a second current amplitude less than said first current amplitude, a second pulse width less than said first pulse width, a second frequency less than said first frequency, a second on-time less than said first on-time, a second off-time greater than said first off-time, a second number of pulses per burst less than said first number of pulses per burst, a second interburst period greater than said first interburst period, and a second interpulse interval greater than said first interpulse interval.

In yet an another embodiment, the action in response to the step of determining whether or not the electrical signal therapy limit is exceeded may comprise providing a third, enhanced electrical signal therapy that, in turn, comprises a pulsed electrical signal defined by at least one parameter selected from the group consisting of a third current amplitude greater than said first current amplitude, a third pulse width greater than said first pulse width, a third frequency greater than said first frequency, a third on-time greater than said first on-time, a third off-time less than said first off-time, a third number of pulses per burst greater than said first number of pulses per burst, a third interburst period less than said first interburst period, and a third interpulse interval less than said first interpulse interval.

Algorithms for determining the at least one neurostimulation parameter discussed above can be stored in memory 217 as a function of the at least one electrical signal therapy limit, the magnitude by which the limit is (or is not) exceeded, or other properties.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230, may comprise a lithium/thionyl chloride cell or a lithium/carbon monofluoride cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2A.

In one embodiment, the communication unit 260 can transmit a log of stimulation data to the patient, a physician, or another party.

The IMD 200 is capable of delivering stimulation that can be intermittent, periodic, random, sequential, coded, and/or patterned. The stimulation signals may comprise an electrical stimulation frequency of approximately 0.1 to 2500 Hz. The stimulation signals may comprise a pulse width of in the range of approximately 1-2000 micro-seconds. The stimulation signals may comprise current amplitude in the range of approximately 0.1 mA to 10 mA. Stimulation may be delivered through either the cathode (−) electrode or anode (+) electrode. In one embodiment, the various blocks illustrated in FIG. 2A may comprise software unit, a firmware unit, a hardware unit, and/or any combination thereof. The stimulation delivered by the IMD 200 in the absence of patient-initiated electrical signal may be referred to herein as "normal operations" or "normal operating mode."

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field.

The magnetic field detection unit 270 may comprise various sensors, such as a Reed Switch circuitry, a Hall Effect sensor circuitry, and/or the like. The magnetic field detection unit 270 may also comprise various registers and/or data transceiver circuits that are capable of sending signals that are indicative of various magnetic fields, the time period of such fields, etc. In this manner, the magnetic field detection unit 270 is capable of detecting whether the detected magnetic field relates to an inhibitory input or an excitory input from an external source. The inhibitory input may refer to an inhibition of, or a deviation from, normal stimulation operation. The excitory input may refer to additional stimulation or deviation from normal stimulation.

One or more of the blocks illustrated in the block diagram of the IMD 200 in FIG. 2A, may comprise hardware units, software units, firmware units, or any combination thereof. Additionally, one or more blocks illustrated in FIG. 2A may be combined with other blocks, which may represent circuit hardware units, software algorithms, etc. Additionally, one or more of the circuitry and/or software units associated with the various blocks illustrated in FIG. 2A may be combined into a programmable device, such as a field programmable gate array, an ASIC device, etc.

Figure 3:
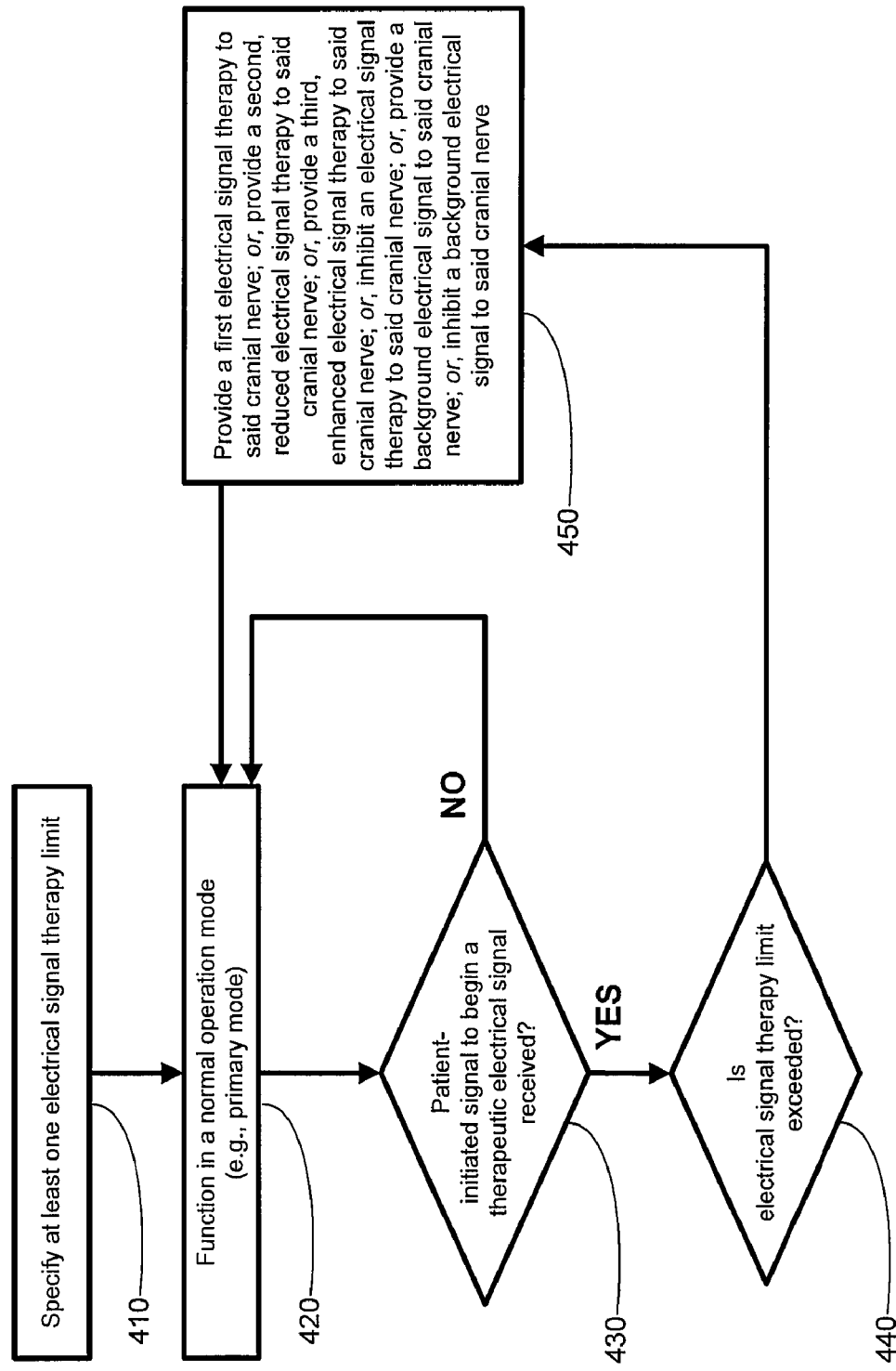
FIG. 3 illustrates a flowchart depiction of a method for performing limited patient-initiated electrical signal therapy, in accordance with an illustrative embodiment of the present invention.

Methods of applying alternative stimulation may include applying a patient-initiated electrical signal mode alone or in combination with background stimulation. Turning now to FIG. 3, a flowchart depiction of a method for limiting patient-initiated electrical signal therapy in accordance with one illustrative embodiment of the present invention is provided. At least one electrical signal therapy limit is specified (block 410) prior to normal operation, such as primary mode operation, of the IMD 200 (block 420). The normal operation mode calls for predetermined delivery of stimulation signals. The IMD 200 may then check to determine whether a patient-initiated signal to administer patient-initiated electrical signal therapy has been received (block 430). If an input to administer patient-initiated electrical signal therapy has not been received, normal operation of the IMD and delivery of stimulation signal is resumed, as indicated in FIG. 3.

However, if it is determined that an input signal prompting administration of patient-initiated electrical signal therapy has been detected, the IMD 200 may determine whether the at least one electrical signal therapy limit has been exceeded (block 440).

Depending on whether the at least one electrical signal therapy limit was or was not exceeded, the IMD 200 may perform patient-initiated electrical signal therapy. Performing may involve one or more of the following:

provide a first electrical signal therapy to said cranial nerve; or, provide a second, reduced electrical signal therapy to said cranial nerve; or, provide a third, enhanced electrical signal therapy to said cranial nerve; or, inhibit an electrical signal therapy to said cranial nerve; or, provide a background electrical signal to said cranial nerve; or, inhibit a background electrical signal to said cranial nerve.

The word "or" is used in the inclusive sense.

After performing patient-initiated electrical signal therapy as described above, the IMD 200 returns to normal operation mode (block 420).

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method of electrical signal therapy provided by an implantable medical device (IMD) to a cranial nerve of a patient, comprising:
specifying an electrical signal parameter threshold; wherein said electrical signal parameter is specific to the electrical signal therapy; and
wherein said threshold is selected from the group consisting of a maximum number of patient-initiated signals to provide a therapeutic electrical signal per a time period, a maximum dose of therapeutic electrical signals per a time period, a maximum duration of the therapeutic electrical signals per a time period, a maximum rate of change of the number of patient-initiated signals to provide a therapeutic electrical signal per a time period, a maximum rate of change of the dose of the therapeutic electrical signal per a time period, and a maximum rate of change of the duration of the electrical signal therapy per a time period,
receiving an input from said patient to enter an alternative mode of electrical signal therapy; wherein said alternative mode of electrical signal therapy comprises altering the electrical signal parameter of the electrical signal therapy and wherein said input from said patient to enter said alternative mode of electrical signal therapy also prompts a temporary interruption from a normal stimulation mode of electrical signal therapy provided by the IMD;
determining whether to implement said alternative mode of electrical signal therapy based on said electrical signal parameter threshold,
and performing said alternative mode of electrical signal therapy when said electrical signal parameter of said alternative mode of electrical signal therapy is below said threshold, and
not performing said alternative mode of electrical signal therapy when said electrical signal parameter of said alternative mode of electrical signal therapy is above said threshold, to inhibit the patient initiated electrical signal therapy provided by the IMD to the cranial nerve of the patient.

2. The method of claim 1, wherein said performing the alternative mode of electrical signal therapy is selected from the group consisting of providing a first electrical signal therapy to said cranial nerve, providing a second, reduced electrical signal therapy to said cranial nerve, providing a third, enhanced electrical signal therapy to said cranial nerve, and providing a background electrical signal to said cranial nerve.

3. The method of claim 1, wherein not performing said alternative mode comprises an action selected from the group consisting of inhibiting an electrical signal therapy to said cranial nerve and inhibiting a background electrical signal to said cranial nerve.

4. A method for limiting patient-initiated electrical signal therapy provided by an implantable medical device (IMD) to a cranial nerve of a patient, comprising:
specifying at least one electrical signal therapy limit selected from the group consisting of a maximum number of patient-initiated signals to provide a therapeutic electrical signal per a time period, a maximum dose of the therapeutic electrical signal per a time period, a maximum duration of the therapeutic electrical signal per a time period, a maximum rate of change of the number of patient-initiated signals to provide a therapeutic electrical signal per a time period, a maximum rate of change of the dose of the therapeutic electrical signal per a time period, and a maximum rate of change of the duration of the electrical signal therapy per a time period;
receiving a patient-initiated signal to begin a patient-initiated therapeutic electrical signal, wherein the patient-initiated therapeutic signal prompts a temporary interruption from a normal stimulation mode of electrical signal therapy;
determining whether or not said patient-initiated electrical signal therapy limit will be exceeded if said receiving the patient-initiated signal to begin the patient-initiated electrical signal therapy is implemented;
performing an action when said limit is not exceeded, said action selected from the group consisting of providing an electrical signal therapy to said cranial nerve, providing a reduced electrical signal therapy to said cranial nerve, providing an enhanced electrical signal therapy to said cranial nerve and providing a background electrical signal to said cranial nerve; and
performing a different action when said limit is exceeded, said different action selected from the group consisting of inhibiting said patient-initiated electrical signal therapy to said cranial nerve.

5. The method of claim 4, further comprising determining a characteristic of said patient-initiated signal, wherein the patient-initiated signal is a magnetic field, comprising determining at least one of a duration of said magnetic field and a magnitude of said magnetic field, and wherein said characteristic is used in determining whether or not said electrical signal therapy limit is exceeded.

6. The method of claim 4, further comprising determining a characteristic of said patient-initiated signal, wherein the patient-initiated signal is a tap input, comprising determining a number of tap inputs received, and wherein said characteristic is used in determining whether or not said electrical signal therapy limit is exceeded.

7. The method of claim 4, wherein the at least one electrical signal therapy limit is specified for at least one time period.

8. The method of claim 7, wherein said at least one time period has a duration from about 10 sec to about 720 hr.

9. The method of claim 7, wherein the at least one electrical signal therapy limit is specified for a plurality of time periods.

10. The method of claim 4, wherein providing a first electrical signal therapy comprises providing a pulsed electrical signal defined by at least one parameter selected from the group consisting of a first current amplitude, a first pulse width, a first frequency, a first on-time, a first off-time, a first number of pulses per burst, a first interburst period, and a first interpulse interval;
wherein providing a second, reduced electrical signal therapy comprises providing a pulsed electrical signal defined by at least one parameter selected from the group consisting of a second current amplitude less than said first current amplitude, a second pulse width less than said first pulse width, a second frequency less than said first frequency, a second on-time less than said first on-time, a second off-time greater than said first off-time, a second number of pulses per burst less than said first number of pulses per burst, a second interburst period greater than said first interburst period, and a second interpulse interval greater than said first interpulse interval; and
wherein providing a third, enhanced electrical signal therapy comprises providing a pulsed electrical signal defined by at least one parameter selected from the group consisting of a third current amplitude greater than said first current amplitude, a third pulse width greater than said first pulse width, a third frequency greater than said first frequency, a third on-time greater than said first on-time, a third off-time less than said first off-time, a third number of pulses per burst greater than said first number of pulses per burst, a third interburst period less than said first interburst period, and a third interpulse interval less than said first interpulse interval.

11. A method for limiting patient-initiated electrical signal therapy provided by an implantable medical device (IMD) to a cranial nerve of a patient, comprising:

specifying at least one limit on patient-initiated electrical signal therapy to a the cranial nerve of a the patient;

wherein the at least one limit is selected from the group consisting of a maximum number of patient-initiated signals to provide a therapeutic electrical signal per a time period, a maximum dose of the therapeutic electrical signal per a time period, a maximum duration of the therapeutic electrical signal per a time period, a maximum rate of change of the number of patient-initiated signals to provide a therapeutic electrical signal per a time period, a maximum rate of change of the dose of the therapeutic electrical signal per a time period, and a maximum rate of change of the duration of the electrical signal therapy per a time period;

receiving a patient-initiated signal to provide an electrical signal therapy to a the cranial nerve, wherein the patient-initiated signal prompts a temporary interruption from a normal stimulation mode of electrical signal therapy provided by the IMD;

determining whether or not said at least one limit on patient-initiated therapy is exceeded by said step of receiving the a patient-initiated signal;

providing the patient-initiated electrical signal therapy to said cranial nerve of the patient if said at least one limit is not exceeded by said step of receiving a the patient-initiated signal; and not providing the patient-initiated electrical signal therapy to said cranial nerve of the patient if said at least one limit is exceeded by said step of receiving a the patient-initiated signal, wherein not providing the patient-initiated electrical signal therapy comprises inhibiting patient initiated electrical signals to said cranial nerve of the patient.

12. The method of claim 11, wherein receiving said patient-initiated signal comprises receiving at least one of a tap input or a magnetic input.

13. The method of claim 11, wherein the at least one electrical signal therapy limit is specified for at least one time period.

14. The method of claim 11, wherein said step of providing the electrical signal therapy if said at least one limit is not exceeded comprises providing a pulsed electrical signal defined by at least one parameter selected from the group consisting of a current amplitude, a pulse width, a frequency, an on-time, an off-time, a number of pulses per burst, an interburst period, and an interpulse interval.

15. The method of claim 13, wherein said time period has a duration from about 10 sec to about 720 hr.

* * * * *